(12) United States Patent  
Angelsen et al.

(10) Patent No.: US 7,699,782 B2  
(45) Date of Patent: Apr. 20, 2010

(54) EXTENDED, ULTRASOUND REAL TIME 3D IMAGE PROBE FOR INSERTION INTO THE BODY

(76) Inventors: Bjørn A. J. Angelsen, Buggs, veg 4b, N7051 Trondheim (NO); Tonni F. Johansen, Nils Uhlin Hansens, veg 50C, N7026 Trondheim (NO)

( * ) Notice: Subject to any disclaimer, the term of this patent is extended or adjusted under 35 U.S.C. 154(b) by 1269 days.

(21) Appl. No.: 11/075,929

(22) Filed: Mar. 9, 2005

(65) Prior Publication Data

US 2005/0203396 A1    Sep. 15, 2005

Related U.S. Application Data

(60) Provisional application No. 60/551,681, filed on Mar. 9, 2004.

(51) Int. Cl.
*A61B 8/00* (2006.01)
*A61B 8/14* (2006.01)

(52) U.S. Cl. .................. 600/444; 600/459; 600/466

(58) Field of Classification Search .................. None
See application file for complete search history.

(56) References Cited

U.S. PATENT DOCUMENTS

| 4,802,487 | A | * | 2/1989 | Martin et al. | ............... 600/463 |
|---|---|---|---|---|---|
| 5,271,402 | A | * | 12/1993 | Yeung et al. | ................ 600/437 |
| 5,651,366 | A | * | 7/1997 | Liang et al. | ................. 600/439 |
| 5,699,805 | A | | 12/1997 | Seward et al. | |
| 5,762,066 | A | * | 6/1998 | Law et al. | ................... 600/439 |
| 6,645,150 | B2 | * | 11/2003 | Angelsen et al. | ........... 600/459 |
| 2002/0045827 | A1 | * | 4/2002 | Powers et al. | ............... 600/447 |
| 2003/0163046 | A1 | * | 8/2003 | Nohara et al. | ............... 600/443 |
| 2005/0090740 | A1 | * | 4/2005 | Raitzer et al. | ............... 600/437 |
| 2005/0203416 | A1 | * | 9/2005 | Angelsen et al. | ............ 600/463 |

* cited by examiner

*Primary Examiner*—Long V Le
*Assistant Examiner*—Angela M Hoffa
(74) *Attorney, Agent, or Firm*—Cohen Pontani Lieberman & Pavane LLP

(57) ABSTRACT

An ultrasound imaging probe for real time 3D ultrasound imaging from the tip of the probe that can be inserted into the body. The ultrasound beam is electronically scanned within a 2D azimuth plane with a linear array, and scanning in the elevation direction at right angle to the azimuth plane is obtained by mechanical movement of the array. The mechanical movement is either achieved by rotation of the array through a flexible wire, or through wobbling of the array, for example through hydraulic actuation. The probe can be made both flexible and stiff, where the flexible embodiment is particularly interesting for catheter imaging in the heart and vessels, and the stiff embodiment has applications in minimal invasive surgery and other procedures. The probe design allows for low cost manufacturing which allows factory sterilized probes to be disposed after use.

30 Claims, 12 Drawing Sheets a)

b)

c)

EXTENDED, ULTRASOUND REAL TIME 3D IMAGE PROBE FOR INSERTION INTO THE BODY

RELATED APPLICATIONS

This application claims priority from U.S. Provisional Patent Application Ser. No. 60/551,681 which was filed on Mar. 9, 2004.

BACKGROUND OF THE INVENTION

1. Field of the Invention

The invention relates to methods, ultrasound probes, and instrumentation for real time 3D imaging around the tip of an ultrasound probe that can be inserted into the body, either through natural openings or through surgical wounds.

2. Description of the Related Art

Real time (Rt) three-dimensional (3D) ultrasound imaging around the tip of a flexible ultrasound probe is in many situations a sought after tool, both for diagnosis and for guidance of procedures. Examples of such procedures are placement of devices in the heart ventricles and atria, guidance of electrophysiology ablation, or guidance in minimal invasive surgery. In these cases, the ultrasound probe gets in direct contact with the blood path, and it is then a great advantage to use factory-sterilized, disposable probes. This requires that the manufacturing cost of the probes can be kept low.

Such 3D imaging around a probe tip is done by scanning a pulsed ultrasound beam in the two angular directions in front of the probe. This type of scanning is ideally done with a two-dimensional matrix array where the element width is less than $\lambda/2$ in both directions, where $\lambda$ is the wave-length of the ultrasound in the tissue. However this gives a large amount of small elements, that either requires an impractically thick cable connecting the array and the instrument, or requires a large amount of beam forming electronics at the probe tip close to the array, which is expensive and space consuming to be used with probes that are inserted into the body. The small size of the elements of the matrix probe also makes it difficult to manufacture the matrix arrays for ultrasound frequencies above 7 MHz.

There is further a need for the probe to be flexible, for example for insertion into the vessels and the heart as a catheter. In this situation one could also want to control flexing of the tip from the external instrument. In other situations, like endoscopic surgery, one would like to have a stiff probe.

SUMMARY OF THE INVENTION

The present invention provides a solution to these problems by combining electronic and mechanical direction steering of the ultrasound beam. Electronic beam forming and scanning within an azimuth 2D plane can be obtained by a linear phased, curvilinear switched, or linear switched array. The ultrasound beam is further scanned in the elevation direction at right angle to the 2D azimuth plane, through mechanical movement of the array. Example embodiments of such mechanical scanning are shown by rotation of the array by a flexible cable through the probe, or mechanical wobbling of the array, for example by hydraulic means.

For limited movement velocity of the imaging object, one can obtain dynamic focusing of the ultrasound beam in the elevation direction by linear combination of the received RF signal from neighboring 2D azimuth scans. Dynamic focusing in the elevation direction, can also be obtained by dividing the array elements in the elevation direction, with for example a switched aperture focusing, or a steerable or switchable signal delay based focusing. To minimize the number of wires that connect the array and the external imaging instrument, the elevation focusing is done by electronics at the tip of the probe. Sub-aperture beam forming in the azimuth direction by electronics at the tip of the probe, also provides a reduction in the number of wires connecting the imaging probe tip and the external imaging instrument.

The probes can be made both flexible and stiff, for best adaption to the application. The tip of the flexible probe can be direction steered (flexed) through wires along the periphery of the probe that are stretched/released through handles at the outside instrument.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
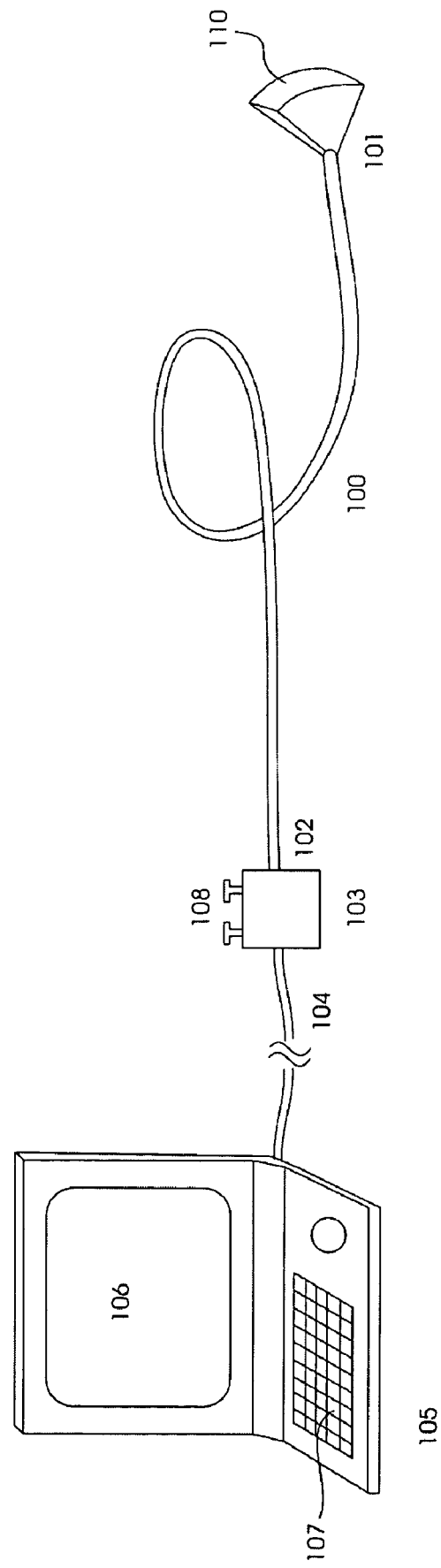
FIG. 1 shows an overview of a real time 3D imaging system with an probe according to the invention.

The invention relates to an ultrasound real time 3D imaging system, which in a typical embodiment is composed of the components shown in FIG. 1, where 100 shows an elongated imaging probe with a distal imaging tip 101 and a proximal end 102 that is connected to an utility console interface 103. The imaging ultrasound beam is transmitted from the distal tip of the probe enabled to be scanned within a three-dimensional (3D) region 110 to be imaged. The utility interface further connects via the cable 104 the probe signals to an ultrasound imaging instrument 105. The imaging instrument has an image display screen 106 for visualization of the images and also other information, and a key board interface 107 for user control of the instrument.

In this particular embodiment, the imaging probe 100 is a particularly flexible catheter probe for example allowing double curving of the probe, which has advantages for imaging inside tortuous vessels and the heart cavities. In other applications, the probe can be much less flexible, close to stiff, for example in minimally invasive surgery where the probes would be inserted through a trocar. For the flexible probe, one often would stretch wires along the periphery of the probe, where the wires can systematically be manipulated by control organs 108 at the utility interface 103 for flexing the tip of the probe in one or two directions.

The invention specially relates to methods of scanning the ultrasound beam within the region 110 of 3D space, from the distal tip of such an elongated probe.

Figure 2:
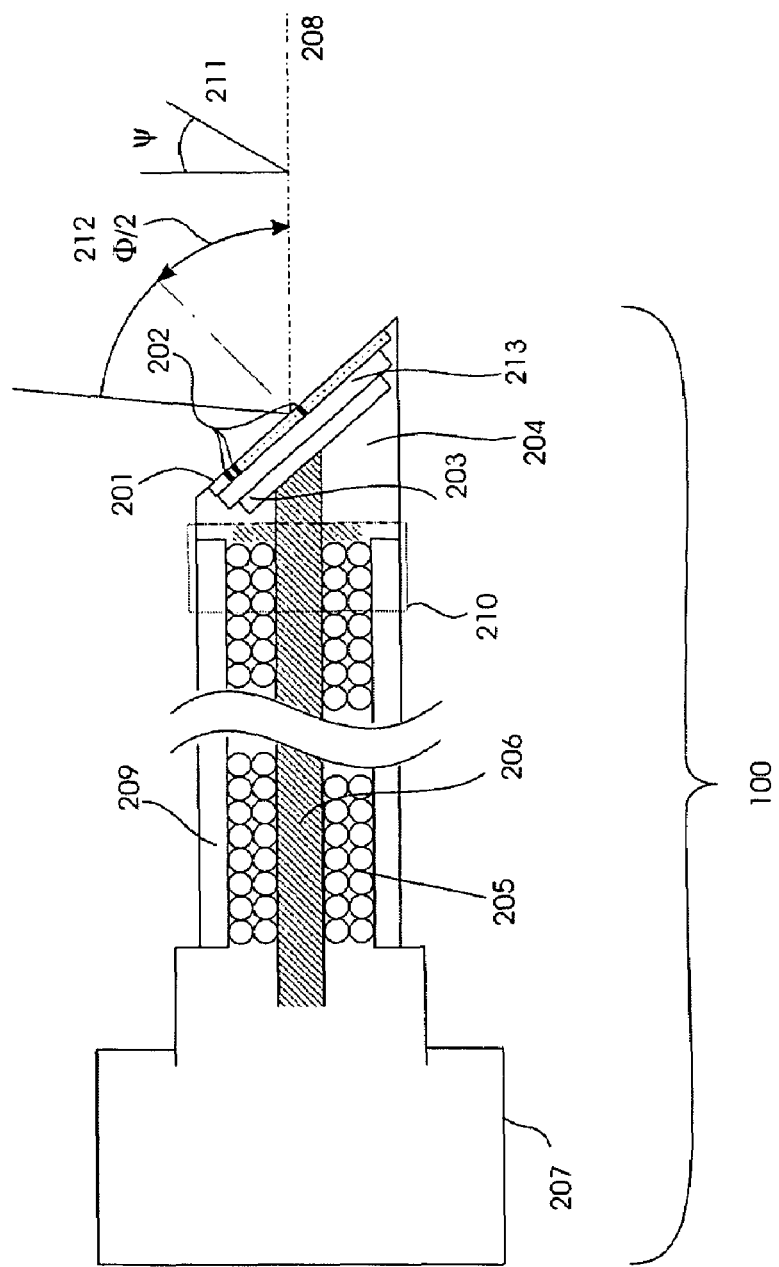
FIG. 2 shows an example embodiment of the distal tip of a flexible, probe according to the invention where the 3D steering of the beam is obtained by electronic steering of the beam within a 2D azimuth sector by an array transducer with additional mechanical rotation of the array.

FIG. 2 shows a first example embodiment according to the invention of the distal tip 101 of such an elongated probe 100. FIG. 2 shows an array transducer 201 which typically can be a linear phased array transducer with a set of array elements 202, or the array can also for example be a switched array or a curved switched array. The array elements 202 are electrically connected to an electronic circuit 203, with an acoustically isolating material (backing material) 213 between the array and the circuit, to avoid ringing acoustic pulses from the back side of the array. The circuit 203 typically contains receiver amplifiers with switching circuits between transmit and receive of the ultrasound pulses. In some embodiments it can also contain steerable or selectable delay circuits of the receive element signals to combine the signals from neighboring elements in sub-aperture groups into a reduced number of sub-aperture signals, so that the connection of the signals between the array and the utility console can be obtained by less number of wires than the total number of elements in the array aperture, as described in relation to FIG. 6a. When the imaging object has limited movement velocity, the number of wires between the imaging tip and the external imaging instrument can also be reduced with synthetic aperture techniques, as further described below in relation to FIG. 6c. This is important to reduce the diameter of the catheter.

The array 201 and the circuit 203 are mounted in an array holder unit 204 that is connected to a flexible rotation cable 205 typically made of double helix spun wires, like a speedometer wire. The rotation cable 205 has a core of electric cable wires 206 that connects the array and circuit to the external utility console 103, as shown in FIG. 1. The wire is on the distal end connected to a motor 207 in the utility console, and transmits the motor rotation to rotation of the transducer array 201 around the cable axis 208. The rotating cable would typically be covered with a plastic sheath 209, but this sheath could in some embodiments be left out. One should note that in some embodiments, the electronic circuit 203 can also be left out, and the cable wires 206 would then connect directly to the array elements 202.

For accurate sensing of the angular direction of the array, a position sensor 210 would typically be mounted at the probe tip to measure the rotation $\psi$, indicated as 211, of the array holder 204 and array 201 in relation to the catheter sheath 209. This position sensor could typically be of optical types like described in FIGS. 10 and 11, but other methods like electromagnetic angular position sensors could also be used. Accurate monitoring of the angular direction of the array is used in the image reconstruction to minimize the effect of variable angular rotation differences along the cable 205 from the proximal to the distal end, as these differences might vary with rotation angle and bending of the probe.

Other position sensors that relate the rotation to a more global reference, like the patient surface, for example using electromagnetic induction, can also be used. Such sensors are well known to any-one skilled in the art.

Figure 3:
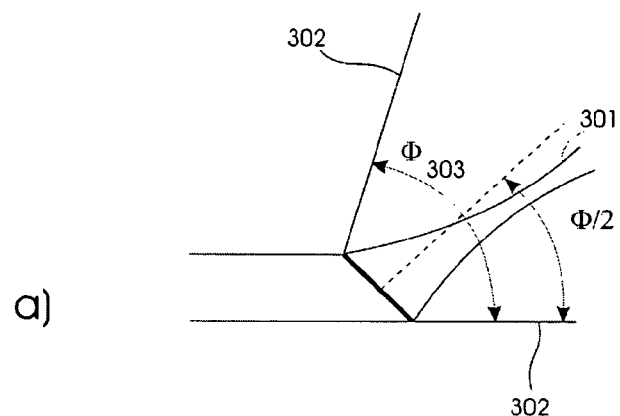
FIG. 3 shows examples of three types of arrays for 2D azimuth scanning of the beam with their corresponding image formats.
Figure 3:
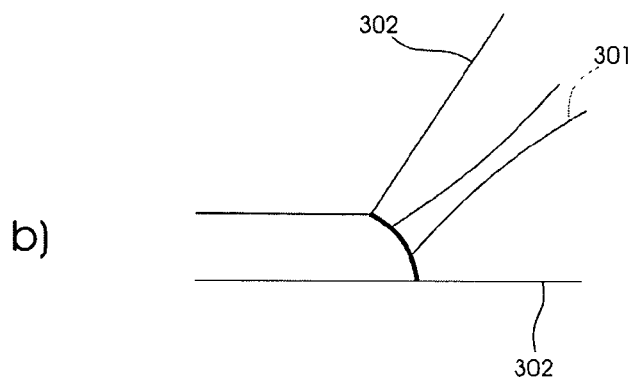
Figure 3:
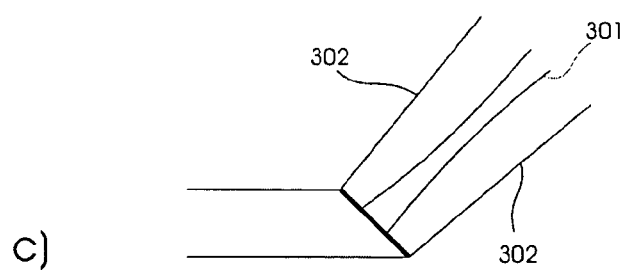

With a linear array embodiment of the array 201, one can obtain electronic direction steering of the ultrasound beam in a sector format with phased array operation as illustrated in FIG. 3a. The full opening angle of the sector scan is $\Phi$, indicated by 303. Beam steering in a weakly opened sector with a switched linear curved array as illustrated in FIG. 3b can also be used. With wide band transducers, for example as shown in U.S. Pat. No. 6,645,150, or U.S. patent application Ser. No. 10/180,990, one could use an array as a phased, sector steered array in a low frequency band where the element pitch is $\sim\lambda/2$, where $\lambda$ is the ultrasound wave length in the tissue, and as a switched array in a high frequency band where the element pitch is $\sim\lambda$. Beam steering in a rectangular format with a switched linear array as illustrated in FIG. 3c is then interesting for high frequencies.

In all of these Figures 301 indicates the ultrasound beam for a particular beam direction, and 302 indicates the boundaries of a typical 2D image format, which is obtained with electronic scanning of the beam.

Figure 4:
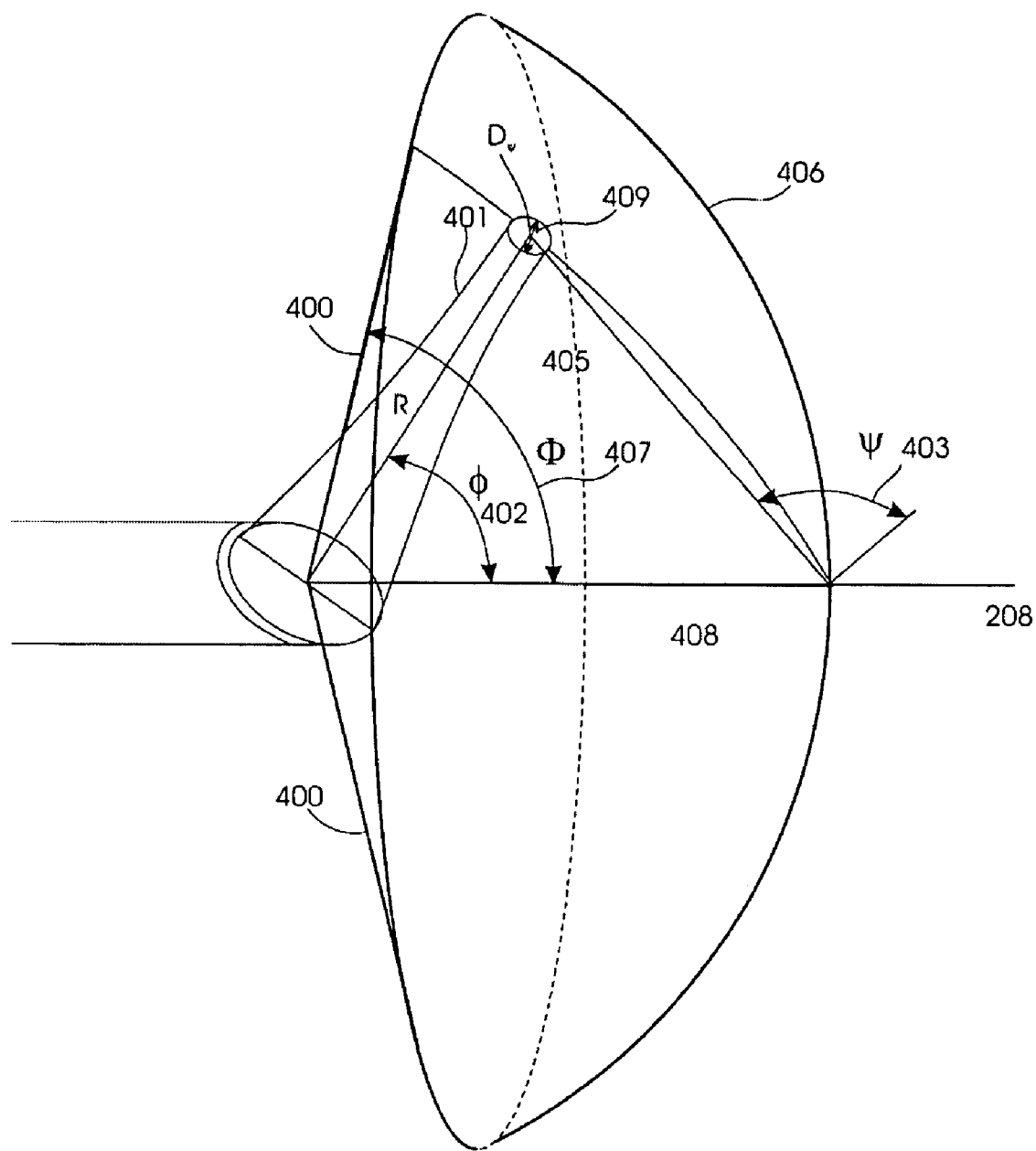
FIG. 4 shows an example of a 3D region that can be scanned by an ultrasound beam from the distal probe tip of the type shown in FIG. 2.

For 3D imaging, the array is rotated around the axis 208, as illustrated in FIG. 4. This Figure illustrates a typical beam 401 obtained with simultaneous electronic steering of the beam with a phased array in the 2D sector format in FIG. 3a, and mechanical rotation of the array. The phased array beam steering provides a beam angle $\phi$ (402) relative to the rotation axis of the array. The mechanical rotation of the array gives a beam angle $\psi$ (403) relative to a reference.

The combined electronic and mechanical direction steering of the beam, allows collection of ultrasound backscatter data from a sub-spherical region with boundaries 400 determined by the 2D sector 405 and the spherical range of the 2D image 406. With an opening angle $\Phi$ (407) of the 2D sector, one could ideally mount the array with a skewed angle to the probe axis 208, so that the normal of the array forms an angle $\Phi/2$ to the probe axis, shown as 212 in FIG. 2. The 3D beam along the probe axis is then obtained with steering of the beam to the outer right side 408 of the 2D sector, and this beam direction can be obtained with all mechanical angular directions $\psi$ of the array, due to the degeneration of the spherical to rectangular coordinate transform for this polar direction. As the ultrasound beam has a certain width determined by the beam focusing and the diffraction, one then can shoot less 2D beams in the directions for small values of $\phi$, than for large values of $\phi$.

Hence, all 2D sectors contain ultrasound beams with large angles $\phi$, while smaller values of $\phi$ are only found in selected 2D sectors, so that the beam density is kept approximately constant in the real 3D space. By example, with a lateral sampling width $D_\psi$ of the beam in the $\psi$ direction at the maximal range R, indicated as 409 in FIG. 4, the number of beams required as a function of $\phi$ for adequate 3D sampling of the image at this angle is $$N(\phi) = 2\pi R \sin\phi / D_\psi \qquad (1)$$

Hence, the fraction of the rotating 2D sectors that has beams at an angle φ is $$\eta(\phi) = N(\phi)/N(\Phi) = \sin\phi/\sin\Phi \quad (2)$$

With a sampling coverage area $A_b$ of the beam at the image range R, given by sampling criteria on the 3D image, one would cover the image area with N beams where $$N_{3D}(\Phi) = 2\pi(1-\cos\Phi)R^2/A_b \quad (3)$$

Typical values are $A_b$=3 mm², R=50 mm, and Φ=π/2, which gives $N_{3D}(\pi/2)$~5200. With 70 μsec per beam, it takes ~370 msec to collect a full 3D frame, i.e. 2.7 3D frames per second. Transmitting a wide beam, and processing 2, 3, or 4 receive beams with small angular differences in parallel for each transmit beam in a known manner, the 3D frame rate can be increased to ~5, 8, or 10 3D frames per second. The frame rate can be further increased by reducing the 3D opening angle Φ, where a reduction to Φ=π/3 reduces the number of beams to $N_{3D}(\pi/3)$=2600 with an increase in the 3D frame rate to 5, 10, 16, and 20, and Φ=π/4 reduces the number of beams to $N_{3D}(\pi/4)$=1500 with an increase in the 3D frame rate to 9, 17, 28, and 38 3D frames per sec for 1, 2, 3, and 4 parallel receive beams respectively. Due to complexities with the mechanical rotation, one would prefer a 3D frame rate 10-20 per sec, which can be achieved with 2 parallel receive beams up to an opening angle of π/3, which is a highly adequate value.

An adequate diameter of such a catheter probe for intra-cardiac echo applications (ICE), is 3 mm. With Φ=π/3, one can use a skewed mounting of the array where the array normal forms an angle π/6 relative to the forward rotation axis 208. This gives a maximal aperture diameter of the array in the 2D azimuth direction of 3/cos(π/6)=3.4 mm. With 64 elements in the phased array, the element pitch becomes ~50 μm, which allows ultrasound wave lengths down to 100 μm corresponding to frequencies up to 15 MHz.

Figure 5:
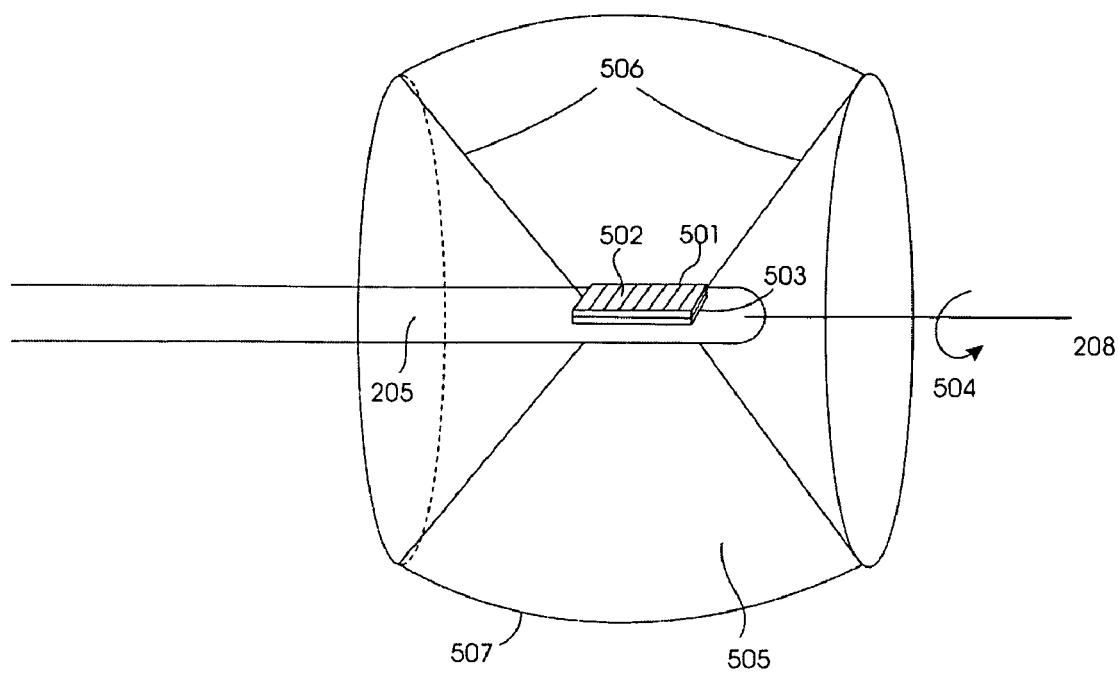
FIG. 5 shows yet another arrangement of a rotating array according to the invention.

A variability of applications using real time 3D imaging, can benefit from different forms of the 3D scanning region, where for example FIG. 5 shows a modification compared to FIG. 2 of the rotating array, where in FIG. 5 the array 501 with elements 502 and an optional electronic circuit 503, is mounted on the side of the flexible, rotating wire shaft 205. Rotating the shaft around its axis 208 for example in the clockwise direction 504, produces a "donut" like 3D scanning region of the ultrasound beam 505 limited by the sector opening lines 506 and the depth range 507. Other arrays like switched linear or curvilinear arrays can also be used. It is also clear that for various purposes, the array can according to the invention be mounted with a variety of angles relative to the rotation axis 208, to provide a variety of 3D scanning regions for a variety of applications.

Figure 6:
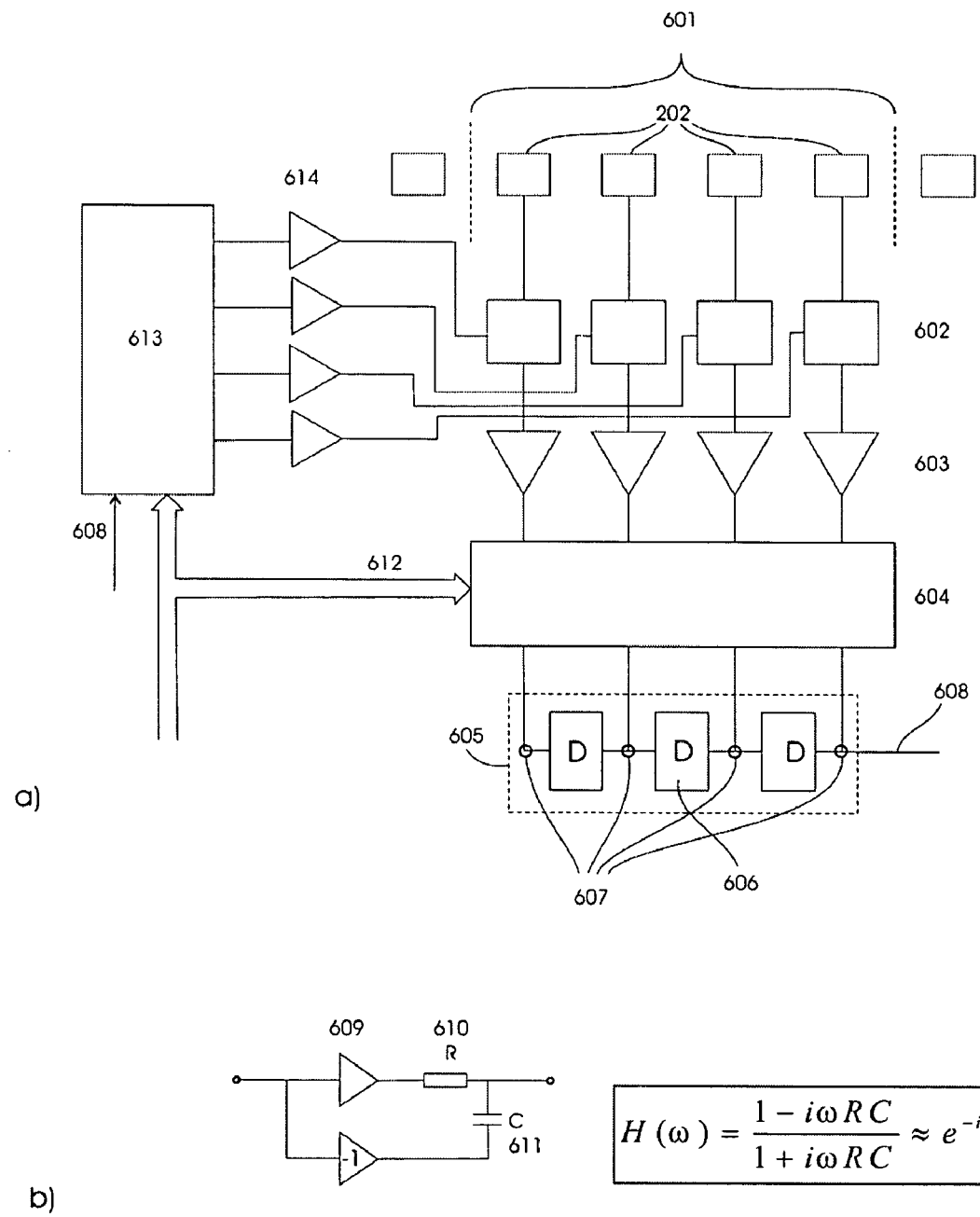
FIG. 6 shows a method of combining the element signals from a sub-aperture group of neighboring elements, to reduce the number of signals that must be connected to the imaging instrument.
Figure 6:
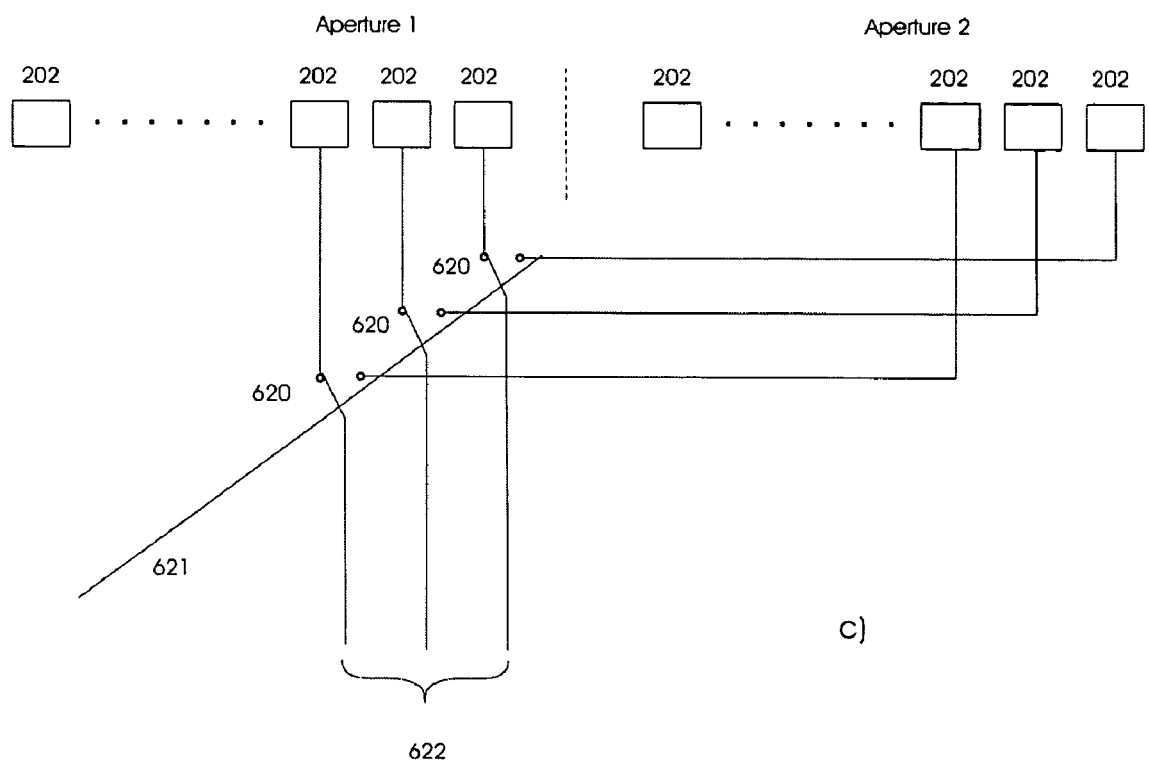

As mentioned above, it is advantageous to use electronic circuits close to the array, for example with amplifiers to maintain signal to noise ratio in reception, but especially with some local sub-aperture beam forming that allows reduction in the number of independent signals that have to be transmitted along the probe. Example embodiments of such sub-aperture beam forming is shown in FIG. 6a, where a group 601 of the array elements 202 forms one of the sub-apertures. In this particular example, the number of elements in the sub-aperture group is 4, but other numbers of 2, 3, etc. can be used.

The signals from each element are fed to transmit/receive switches 602 that in receive mode feed the signal to receiver amplifiers 603. The outputs of the receiver amplifiers are in this example embodiment of sub-aperture processing fed to a cross-point switch 604 that connects the element signals to a summing delay line system 605 with a set of delay elements 606, so that any of the signals can be connected to any delay-point 607. The output 608 of the delay line system is then fed via the cable 206 to the external imaging instrument where the sub-aperture signals are combined to a complete beam, or several parallel beams, according to known methods.

An example embodiment of a delay cell is shown in FIG. 6b, where 609 indicates a differential amplifier, and the signal delay is given by the resistor 610 and capacitor 611. The transfer function of this system is $$H(\omega) = \frac{1 - i\omega RC}{1 + i\omega RC} = e^{-i2\tan^{-1}\omega RC} \approx e^{-i\omega 2RC} \quad (4)$$

which when ω<1/RC gives a signal delay τ=2RC. The actual delay for each element signal is then determined by which summing point 607 the signal is fed into the delay line structure 605 determined by the set-up of the cross point switch 604 that is done via the sub-aperture control bus 612.

The transmit beam of the sub-aperture can in its most general form be generated by a sub-aperture transmit beam former 613 that feeds a set of element driver amplifiers 614 with transmit pulses that have intermediate delays given by the sub-aperture transmit beam former 613 and set up by the sub-aperture control bus 612. The transmit trigger pulse for each sub-aperture transmit beam-former is conveniently transferred on the receive line 608 for each sub-aperture, to limit the number of wires connecting the catheter tip and the imaging instrument.

Figure 7:
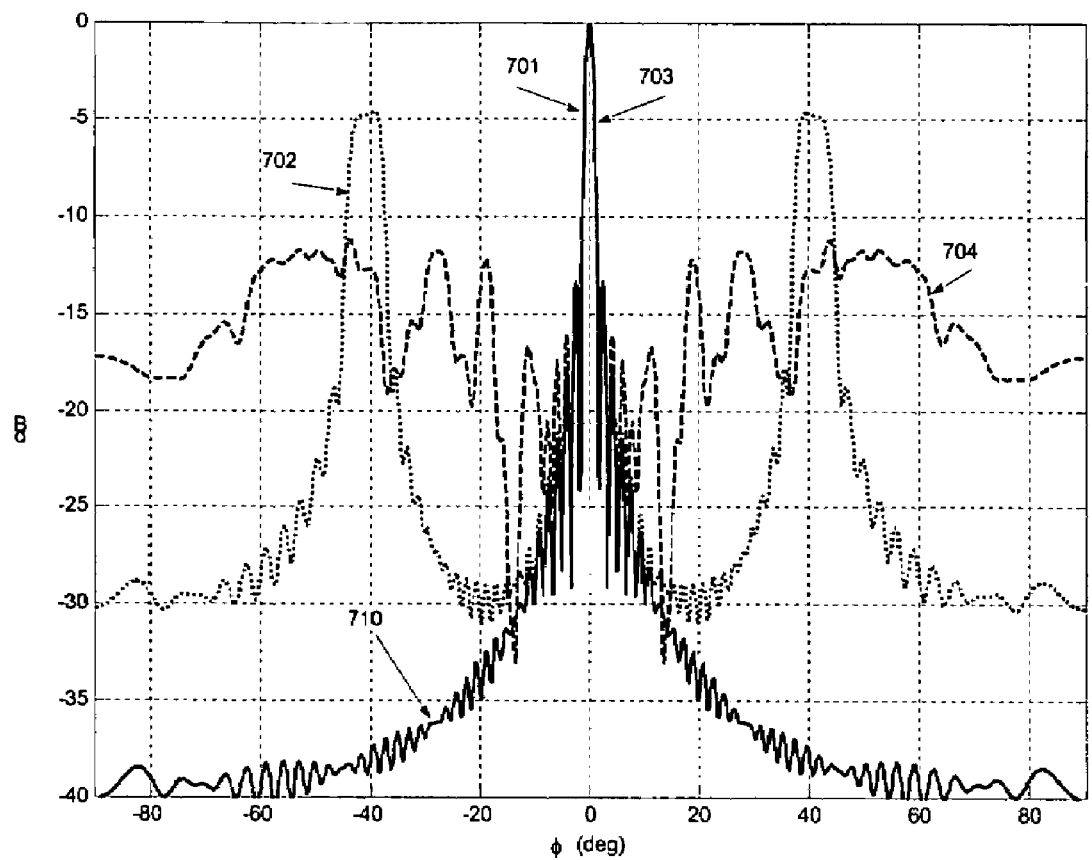
FIG. 7 shows example transmitted beam profiles with grating lobes that is found with transmitting with less than all array elements in a sub-aperture arrangement.

The sub-aperture transmit beam-former can in some applications be left out, where only a sub-set of the elements in the sub-aperture, for example 1 or 2 elements, are used to transmit at each sub-aperture. In these cases, the transmit beam would get grating lobes as illustrated in FIG. 7 for a wide band transmit pulse. This Figure shows the amplitude of the far-field beam profile of the transmitted beam as a function of azimuth angular direction from the beam center axis. In the examples of FIG. 7, each sub-aperture has 3 elements, and a single element is used to transmit from each sub-aperture. 701 shows the main lobe and 702 shows the grating lobes of the beam where the transmit elements have the same position within each sub-aperture (periodic position of the transmit elements). 703 shows the main lobe of the beam where the transmit elements have a close to random variation of their position within each sub-aperture, and 704 shows the side lobes for this random location. We notice that with the random variation of the transmit elements, the sharp peak grating lobe disappears, and we get a more even leveled side lobes which are higher than the side lobes for the transmit elements with a fixed position in each sub-aperture.

The transmit beam grating lobes are also reduced by focusing of the beam. Their effect on the image is further reduced since the receive beam which uses the full sub-apertures is missing these grating lobes, hence attenuating the back scattered signal from these lobes. However, the transmitted grating lobes would generate some noise in the image, and lowest noise images would be obtained with a full sub-aperture transmit beam former, illustrated as 613 in FIG. 6a.

When the imaging object has limited movement velocity, one can also reduce the number of wires connecting the imaging tip and the external instrument with a synthetic aperture method, as illustrated in FIG. 6c. The total array aperture is in this Figure divided in the middle into two, equal groups, Aperture 1 and Aperture 2. The array elements 202 are pair wise from each group connected to 2 to 1 multiplexers 620, which through the control signal 621 connect either the elements from Aperture 1 (as shown in the Figure) or Aperture 2 to the wires 622 that connects through the probe to the external imaging instrument. Switching the multiplexers 620, image beams are in an alternating sequence collected from Aperture 1 and Aperture 2, and then the RF signal for the two beams from Aperture 1 and Aperture 2 are combined with the Synthetic aperture technique known to anyone skilled in the art, into a single beam focused at all depths with focus width determined by the full aperture.

Dynamic focusing of the beam in the elevation direction can be achieved by dividing the array elements in the elevation direction, and feeding the element signals to a sub-aperture beam former like exemplified in FIG. 6a for each azimuth position of the elements. The outputs of the elevation focusing beam formers from neighboring azimuth elements, could then in turn be fed to azimuth sub-aperture beam formers as described. For the elevation focusing, one would only need small delays, as there is no large electronic direction steering of the beam in the elevation direction. Small electronic direction steering is highly interesting to use parallel receive beams in the elevation direction also, to increase the frame rate, in a manner known to anyone skilled in the art.

For the elevation focusing of the transmit beam, one would in most situations avoid the transmit beam former 613 of FIG. 6a and transmit with a central group of elevation elements with a fixed pre-focusing. This gives an adequately elevation focused transmit beam, as the receive focusing provides the dynamic elevation focusing. With parallel elevation beams, the elevation width of the transmit beam must also be sufficiently high.

When the object has limited movement velocity, one can also obtain depth adjusted focusing of the image beam by a synthetic aperture linear combination of the received RF signal of the beams with same azimuth direction from a group of neighboring elevation scans.

Figure 8:
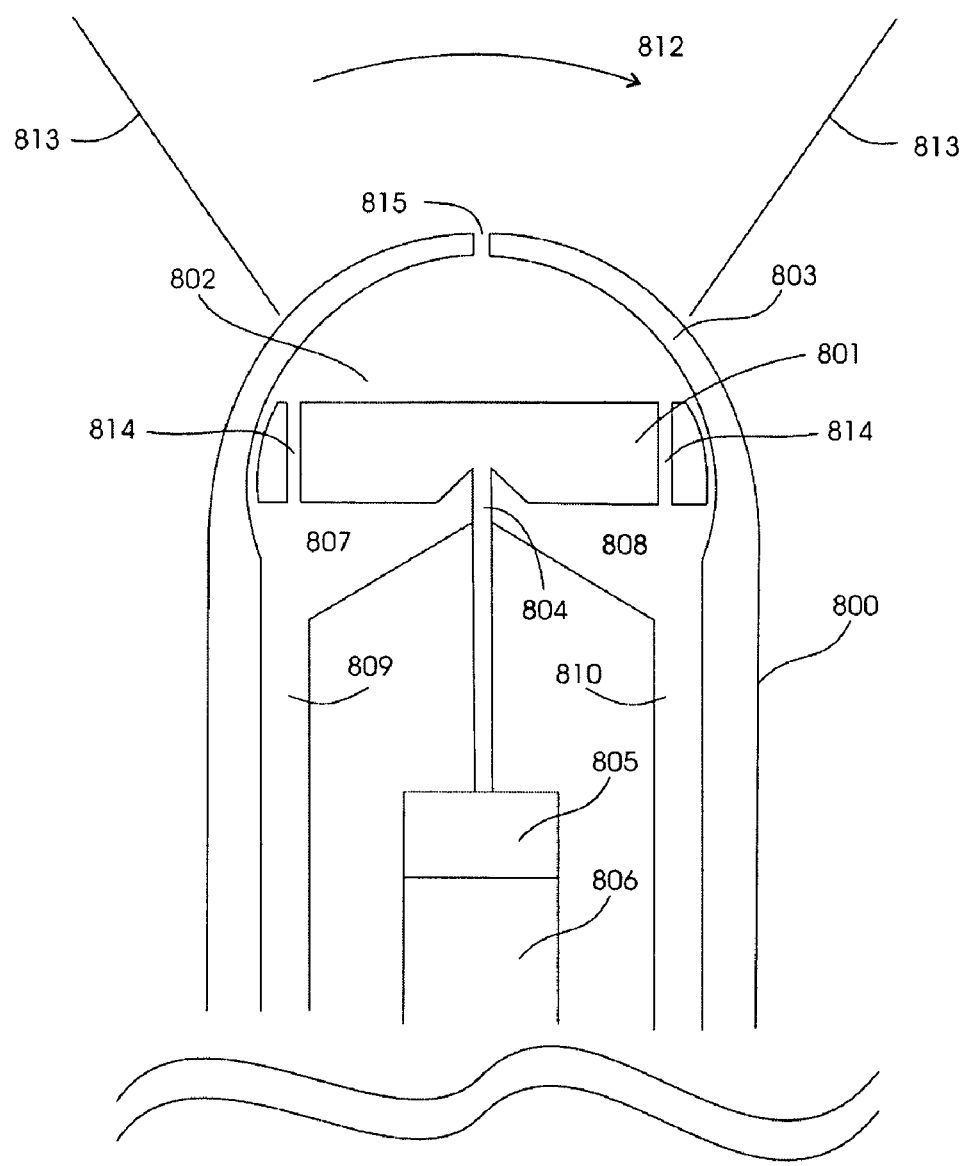
FIG. 8 shows yet another method of 3D scanning of the ultrasound beam from the distal tip of the probe, according to the invention.

Yet another embodiment for 3D scanning of the ultrasound beam according to the invention, is shown in FIG. 8, where 801 shows the combined array and integrated circuit assembly that is enclosed in a sub-spherical dome 803. The assembly 801 is connected to a flexible member 804 that locates the assembly in the middle of the dome and also feeds electric signal wires from the array and electronic circuit to the imaging instrument. The member 804 can for example be made as a printed flex circuit or similar structure. The signal wires can connect to a more convenient type of cable 806 at the interface 805 to be fed throughout the probe to connect to the utility console 103 of FIG. 1.

The probe in this example embodiment contains two hydraulic channels 809 and 810 that can inject or remove fluid from the chambers 807 and 808, that are separated by the flexing member 804. In normal scanning operation, the interior compartments 802, 807, and 808 are filled with a fluid, preferable water with physiological composition. Injecting fluid through the tube 809 into compartment 807 while removing fluid through tube 810 from compartment 808 causes the array/circuit assembly 801 to rotate in the clockwise direction indicated by the arrow 812. The opposite rotation is obtained by injecting fluid through tube 810 into chamber 808 while removing fluid through tube 809 from chamber 807. Using valves at the distal end of the channel, one can also construct designs, where one fluid channel feeds continuously fluid out to the array, and the fluid is either dumped out of the probe at the tip, or returned to the proximal end of the probe through a separate channel.

For simplified filling of the chambers 802, 807, and 808 with fluid, without introducing air bubbles, a continuous forward filling with fluid is obtained by the channels 814 that feeds fluid from the compartments 807 and 808 into the compartment 802, while the channel 815 feeds fluid from the compartment 802 to the outside front of the probe dome. This continuous flow of fluid to the front of the dome, improves acoustic contact between the dome and the object contact surface, or can spill into the blood when the probe is inserted into a blood-filled region. In other embodiments, the draining of the fluid from compartment 802 can be done through the probe to its proximal, outside end, by a specific channel through the probe from the distal to the proximal end.

Figure 9:
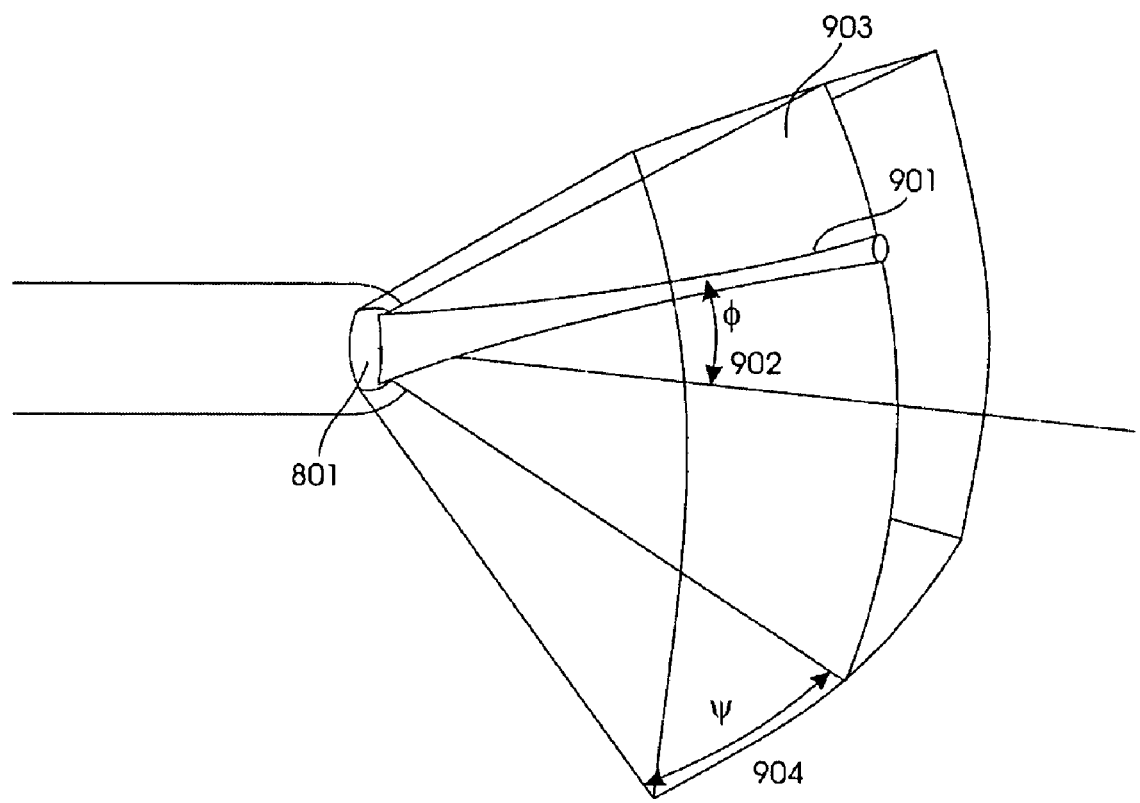
FIG. 9 shows an example of a 3D region that can be scanned with an ultrasound beam generated by the arrangement in FIG. 8.

The probe is on its proximal end connected electrically and hydraulically to the utility console 103 of FIG. 1, which for this embodiment also contains a hydraulic pumping and control system that injects or removes fluid through the channels 809 and 810 and provides the wobbling motion of the array assembly 801. The array can typically be a linear phased array with a 2D azimuth scan normal to the wobbling direction which is in the elevation direction of the 2D scan. This provides a three-dimensional scanning of the ultrasound beam as illustrated in FIG. 9, where 901 indicates an ultrasound transmit/receive beam for the array/circuit assembly 801 with azimuth angle φ illustrated as 902 within a 2D sector 903. The wobbling of the array/circuit assembly 801 provides a steerable elevation angle ψ of the 2D sector and the beam indicated as 904. It should be clear that this hydraulic wobbling mechanism also allows for mounting of the array so that the wobbling axis forms an angle other than 90 deg to the probe tip axis, to adjust the detailed location of the 3D imaging region in relation to the probe tip axis to the particular application at hand.

With a sampling coverage area $A_b$ of the beam at image range R, azimuth scan opening angle of Φ and elevation scan opening angle of Ψ, one would with the scanning method described in FIGS. 8 and 9 require $N_{3D}$ beams where $$N_{3D} = \Phi \Psi R^2 / A_b \tag{5}$$

With $\Phi=\Psi=\pi/2$, R=50 mm and $A_b=3$ mm², a total number of beams to cover the region is $N_{3D}=2056$. With 70 µsec per beam, it takes 144 msec to capture the image, giving ~6 3D frames per second. Using 2, 3, and 4 parallel beams increases the 3D frame rate to 12, 18, and 24 3D frames per second with this opening angle. Reducing the opening angles to $\Phi=\Psi=\pi/3$, decreases the required number of beams to $N_{3D}=914$, increasing the 3D frame rate to ~15, 30, 45, and 60 with 1, 2, 3, and 4 parallel receive beams. This scan method could hence conveniently be used with down to one single parallel receive beam, where the high 3D frame rates are obtained by decreasing the 3D scan opening angle below $(\pi/2)^2$.

Figure 10:
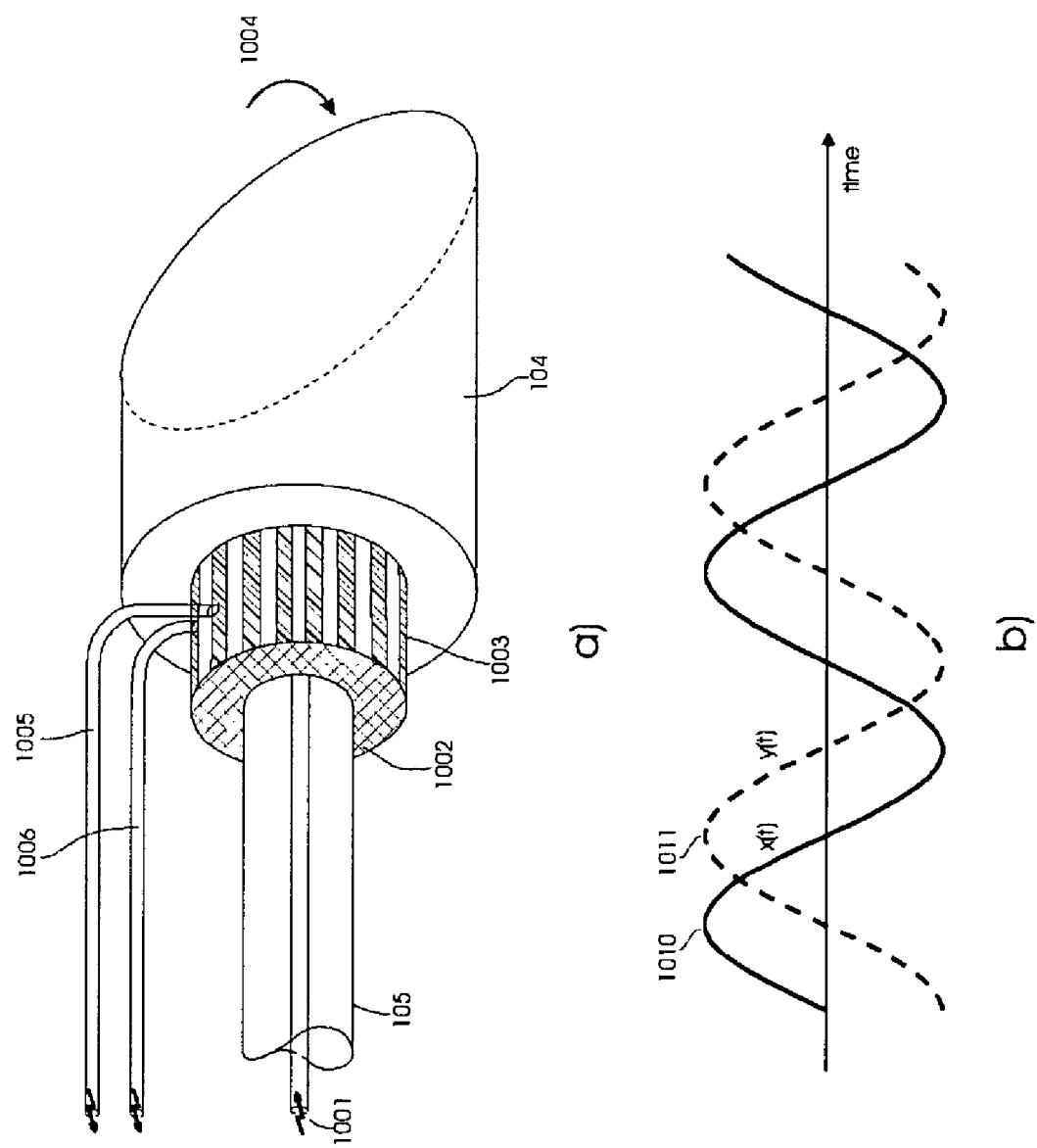
FIG. 10 shows an example of an optical angular position resolver for measuring the mechanical rotation of the array in a probe tip like displayed in FIG. 2.
Figure 11:
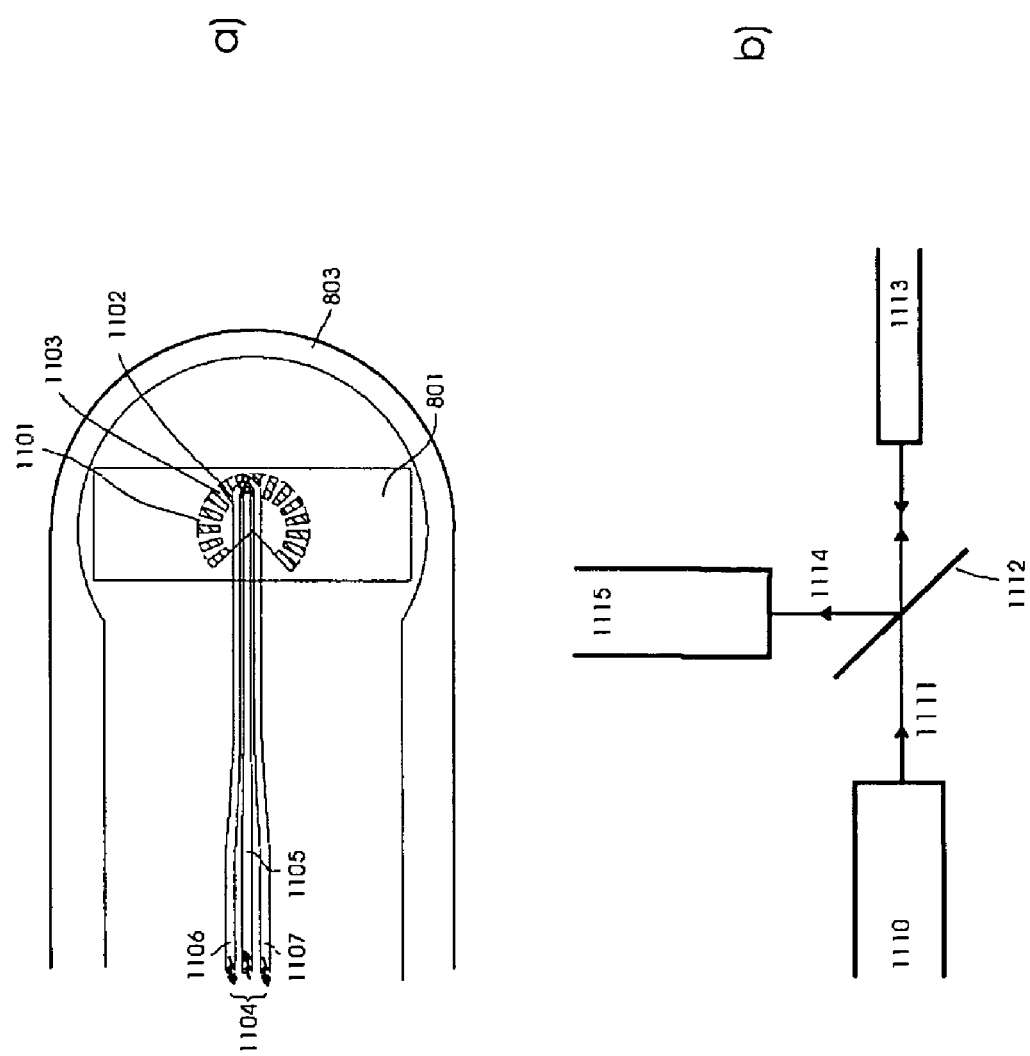
FIG. 11 shows an example of an optical angular position resolver for measuring the angular wobbling of the array for a probe tip of the type shown in FIG. 8.

To avoid geometric distortions of the image in the direction of the mechanical scan, one can conveniently use an angular position sensor of the moving array/circuit assembly at the tip of the probe. Such position sensor can be based on optical or electromagnetic principles according to known methods, and for sake of example FIG. 10 illustrate an optical position sensor for the rotating scan system of FIGS. 2 and 5, and FIG. 11 illustrate an optical position sensor for the wobbling scan system in FIG. 8.

FIG. 10a shows the rotating array holder 104 with the rotating drive cable 105, that rotates the array in the direction indicated by 1004. The rotating drive cable contains in this example embodiment also an optical fiber 1001 that feeds light into a transparent sub-part 1002 of the array holder. The surface of the sub-part 1002 is partly covered with a light inhibiting film at the end face and also at grating lines 1003 in a periodic pattern along the circumference of 1002 that inhibits light to shine out through the circumference, while between the grating lines the light is allowed to shine through. The distance between the grating lines is equal to the width of the grating lines within the accuracy of the manufacturing.

Two optical fibers 1005 and 1006 picks up light that shines through the circumference of 1002 and feeds the light back to the instrument where it is converted to electrical analog signals by for example photo transistors and subsequently converted to digital form for processing to accurately detect the rotational angle of the array holder 104. Example signals after the phototransistors for the two fibers are shown in FIG. 10b where 1010 shows a typical signal x(t) from fiber 1005 and 1011 shows a typical signal y(t) from fiber 1006. Due to spread of the light, the signals are close to sinusoidal in shape. The two fibers 1005 and 1006 have a distance between each other close to ¼ of the period of the grating lines, which gives close to 90 deg phase lag of y(t) in relation to x(t). An accurate resolving of the rotational angle ψ can then for example be found by the following relation $$\psi(t) = F\{x(t), y(t)\} \quad (6)$$

where for many applications F can be approximated by the inverse tangent as $$\psi(t) = F\{x(t), y(t)\} = \tan^{-1}\{y(t)/x(t)\} \quad (7)$$

A similar optical position sensor for the wobbling system in FIG. 8, is shown in FIG. 11a, where 801 shows the array holder within the dome 803. In this example embodiment, a variable reflectance grating 1101 composed of stripes 1102 with high reflectance periodically arranged with stripes 1103 of low reflectance. A triple optical fiber system 1104 containing one fiber 1105 for shining light onto the reflectance grating, and two fibers 1106 and 1107 for transmitting the light reflected from the grating to the instrument. The reflected light is detected and digitized in the instrument as for the position sensor in FIG. 10a. The distance between the pickup areas of fiber 1106 and 1107 is ¼ of the grating period, so that the signals in the two fibers 1106 and 1107 produces signals x(t) and y(t) as in FIG. 10b, which is further processed to resolve the angular position of the array holder similar to Eqs. (6,7).

In FIG. 10a is shown a position sensor with a transmitting grating, while it is clear to any one skilled in the art that a reflecting grating could equally well be used similar to the sensor in FIG. 11a, for which sensor one could also use a transmitting grating.

With two fibers that collects light that is 90 deg out of phase with each other (quadrature phase) one is able to resolve the direction of rotation. If one knows the rotation direction, it would be sufficient to have a single fiber for the reflected light, however, the conversion from light intensity to angle would be simplified by the use of two light signals with quadrature phase relationship.

The same fiber can also be used for transmitted and reflected light using for example a transmitting mirror as shown in FIG. 11b. The light source 1110 shines a light beam 1111 through a transmitting mirror 1112 so that the light enters the fiber 1113. The light reflected at the distal end of the fiber will then come out of the tip and be reflected at the mirror 1112 so that the reflected light is separated into the beam 1114 that hits the detector 1115 and is converted to an electrical signal and digitized.

Other methods of angular position sensing can be based on electromagnetic methods of measuring the array angle in relation to the tip, and also in relation to the external world.

Using wide band or multi-band transducers based on ceramic films as described in U.S. Pat. No. 6,791,692 of Jul. 13, 2004, one can operate the ultrasound transducer both in a low frequency band for an overview image with large penetration, and in a high frequency band for a short range image with improved resolution. The overview image could for example be used to guide one's way in the cardiac chambers to move the probe tip close to an electrophysiology ablation scar, and then evaluate the scar with the high resolution short range image. Similarly could the long range image be used to get an overview of the movement of native heart valves to evaluate best procedure for valve repair or valve replacement, while the short range image can be used to evaluate details in valve morphology.

It is also expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment as a general matter of design choice. It is the intention, therefore, to be limited only as indicated by the scope of the claims appended hereto.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. An ultrasound imaging probe having a distal imaging end to be inserted into a body, and a proximal end, opposite along the probe to said distal end, to be connected to an external ultrasound imaging instrument outside said body, said probe comprising:

an ultrasound transducer array disposed proximate to said distal imaging end, said ultrasound transducer array including means for electronically steering an ultrasound beam in a 2D azimuth plane;

means for mechanically wobbling said ultrasound transducer array in an elevation direction substantially normal to said 2D azimuth plane and to steer said ultrasound beam in said elevation direction in a back and forth manner, wherein said means for mechanically wobbling said ultrasound transducer includes a hydraulic pump mechanism for pumping hydraulic fluid through at least one channel in said probe to thereby wobble the transducer array, and said hydraulic fluid pumped by said hydraulic pump mechanism fills a space around said ultrasound transducer array in said distal probe end to function as an acoustic transmission fluid;

whereby through said combined electronic steering of said ultrasonic beam in said 2D azimuth plane and said mechanical wobbling of said ultrasound transducer array in said elevation direction, said ultrasound beam being steered at a sufficiently dense set of directions in a region of 3D space around said distal end of said probe so that 3D ultrasound imaging of said region appears in substantially real time to a human observer.

2. The ultrasound imaging probe of claim 1, wherein said hydraulic pump mechanism is connected to said proximal end of the probe.

3. The ultrasound imaging probe of claim 2, wherein said distal end contains at least one draining channel for permitting draining of said hydraulic fluid so that a continuous flow of hydraulic fluid around said ultrasonic transducer array may be obtained to remove gas bubbles in said hydraulic fluid around said ultrasound transducer array.

4. The ultrasound imaging probe of claim 3, wherein at least one draining channel channels said hydraulic fluid to the exterior of said distal end.

5. The ultrasound imaging probe of claim 1, wherein said ultrasound transducer array is a linear phased array.

6. The ultrasound imaging probe of claim 5, wherein said ultrasound transducer array includes elements for generating said ultrasound beam, and said elements are divided in said elevation direction for at least one of
transmission of a wide beam with multiple parallel receive beams in said elevation direction within said ultrasonic beam, to increase a frame rate thereof with 3D imaging; and
electronic steering of the focus of said ultrasound beam in said elevation direction.

7. The ultrasound imaging probe of claim 5, further comprising means for depth adjusted focusing of said ultrasound beam in said elevation direction for each azimuth position of the beams by linear combination in said elevation direction of an RF signal in a group of neighboring elevation scans.

8. The ultrasound imaging probe of claim 5, further comprising means for generating multiple receive beams within said transmit beam in said elevation direction for each azimuth position of said transmit beam by linear combination in said elevation scan direction of an RF signal in a group of neighboring elevation scans.

9. The ultrasound imaging probe of claim 1, wherein said ultrasound transducer array is a curved linear switched array.

10. The ultrasound imaging probe of claim 9, wherein said ultrasound transducer array includes elements for generating said ultrasound beam, and said elements are divided in said elevation direction for at least one of
transmission of a wide beam with multiple parallel receive beams in said elevation direction within said ultrasonic beam, to increase a frame rate thereof with 3D imaging; and
electronic steering of the focus of said ultrasound beam in said elevation direction.

11. The ultrasound imaging probe of claim 9, further comprising means for depth adjusted focusing of said ultrasound beam in said elevation direction for each azimuth position of the beams by linear combination in said elevation direction of an RF signal in a group of neighboring elevation scans.

12. The ultrasound imaging probe of claim 9, further comprising means for generating multiple receive beams within a transmit beam in said elevation direction for each azimuth position of said transmit beam by linear combination in said elevation scan direction of an RF signal in a group of neighboring elevation scans.

13. The ultrasound imaging probe of claim 1, wherein said ultrasound transducer array is operable in a phased array mode in a first frequency range, and in a switched array mode in a second frequency range, said second frequency range being higher than said first frequency range.

14. The ultrasound imaging probe of claim 13, wherein said ultrasound transducer array includes elements for generating said ultrasound beam, and said elements are divided in the elevation direction for at least one of
transmission of a wide beam with multiple parallel receive beams in said elevation direction within said ultrasonic beam, to increase a frame rate thereof with 3D imaging; and
electronic steering of the focus of said ultrasound beam in said elevation direction.

15. The ultrasound imaging probe of claim 13, further comprising means for depth adjusted focusing of said ultrasound beam in said elevation direction for each azimuth position of the beams by linear combination in said elevation direction of an RF signal in a group of neighboring elevation scans.

16. The ultrasound imaging probe of claim 13, further comprising means for generating multiple receive beams within a transmit beam in said elevation direction for each azimuth position of said transmit beam by linear combination in said elevation scan direction of an RF signal in a group of neighboring elevation scans.

17. The ultrasound imaging probe of claim 1, further comprising integrated circuits with receiver amplifiers for high sensitivity imaging disposed in said distal end of said probe.

18. The ultrasound imaging probe of claim 1,
wherein said ultrasound transducer array includes elements for generating said ultrasound beam; and
wherein said probe further comprises integrated circuits disposed in said distal end of said probe, and said integrated circuits having receiver amplifiers and delay circuits to combine received signals from neighboring elements into sub-aperture signals, whereby the number of wires connecting said integrated circuits and the external imaging instrument is less than the number of elements in said array.

19. The ultrasound imaging probe of claim 18, wherein a subgroup of said array elements forms said transmission beam.

20. The ultrasound imaging probe of claim 1, further comprising:
an azimuth aperture, which is divided into N equal sub-apertures, where N is at least 2; and
said ultrasound transducer array includes elements for generating said ultrasound beam in said N sub-apertures, wherein elements of equivalent position in said N sub-apertures are coupled to N-to-1 multiplexers;
wherein an output of each of said multiplexers is fed along cable wires to the external imaging instrument; and
wherein said multiplexers are controlled by control signals, so that image beams are in a sequence collected from said N sub-apertures, and
received signals sequentially collected from said N sub-apertures are linearly combined to form a common image beam signal focused to all depths with focus width given by the total aperture;
whereby for imaging of objects with a low movement velocity, the number of wires connecting said distal imaging end and the external imaging instrument may be reduced.

21. The ultrasound imaging probe of claim 1, further comprising an angular position sensor mounted proximate a tip of said distal end of said probe for measuring the wobbling angle of said ultrasound transducer array relative to said probe tip.

22. The ultrasound imaging probe of claim 21, wherein the measured wobbling angle of said ultrasound beams is used in the image reconstruction.

23. The ultrasound imaging probe of claim 1, further comprising a first plurality of electromagnetic sensors for measuring the wobbling position of said ultrasound transducer array, said sensors being mounted to move with the said ultrasound transducer array, in relation to a second plurality of electromagnetic sensors.

24. The ultrasound imaging probe of claim 23, wherein the wobbling position of said ultrasound transducer array is used in the image reconstruction.

25. The ultrasound imaging probe of claim 1, wherein said probe is flexible.

26. The ultrasound imaging probe of claim 25, further comprising at least one wire running along a periphery of said probe from said proximal end thereof to said distal end thereof, whereby selective pulling and releasing of one or more of said wires at said proximal end of the probe, causes direction flexing of said distal end of said probe.

27. The ultrasound imaging probe of claim 1, wherein said ultrasound transducer array is mounted on a flexible member.

28. The ultrasound imaging probe of claim 27, wherein the flexible member is a printed flex circuit.

29. The ultrasound imaging probe of claim 27, wherein said probe includes two channels that can at least one of inject or remove the hydraulic fluid from two respective chambers separated by said flexible member.

30. The ultrasound imaging probe of claim 29, wherein said ultrasound transducer array comprises two channels that allow a continuous feed of the hydraulic fluid to a distal side of said transducer array from said two separate chambers.

* * * * *